(12) United States Patent
Perry et al.

(10) Patent No.: US 7,881,884 B2
(45) Date of Patent: Feb. 1, 2011

(54) FLOWMETER ARRAY PROCESSING ALGORITHM WITH WIDE DYNAMIC RANGE

(75) Inventors: Leslie W. Perry, Kingwood, TX (US); Espen S. Johansen, Humble, TX (US)

(73) Assignee: Weatherford/Lamb, Inc., Houston, TX (US)

( * ) Notice: Subject to any disclaimer, the term of this patent is extended or adjusted under 35 U.S.C. 154(b) by 136 days.

(21) Appl. No.: 12/025,294

(22) Filed: Feb. 4, 2008

(65) Prior Publication Data

US 2008/0189057 A1 Aug. 7, 2008

Related U.S. Application Data

(60) Provisional application No. 60/888,426, filed on Feb. 6, 2007.

(51) Int. Cl.
G01F 1/00 (2006.01)
G01L 27/00 (2006.01)
G06F 7/60 (2006.01)

(52) U.S. Cl. ............................. 702/45; 73/1.59; 703/2

(58) Field of Classification Search .............. 702/45, 702/33, 47–48, 50, 52–54, 57, 79, 81, 138, 702/140, 179, 182, 189–191; 703/2, 5; 73/1.57, 73/1.59, 1.66, 1.82, 1.83, 37, 49.1, 49.5, 73/170.01, 170.11, 170.13, 170.14, 700, 73/703, 861.18, 861.27, 861.42

See application file for complete search history.

(56) References Cited

U.S. PATENT DOCUMENTS

| 6,354,147 | B1 | 3/2002 | Gysling et al. | |
|---|---|---|---|---|
| 6,587,798 | B2 | 7/2003 | Kersey et al. | |
| 6,601,458 | B1 | 8/2003 | Gysling et al. | |
| 6,609,069 | B2 | 8/2003 | Gysling | |
| 6,691,584 | B2 * | 2/2004 | Gysling et al. | 73/861.42 |
| 6,813,962 | B2 * | 11/2004 | Gysling et al. | 73/861.26 |
| 6,889,562 | B2 * | 5/2005 | Gysling et al. | 73/861.42 |
| 7,150,202 | B2 | 12/2006 | Gysling | |
| 7,152,460 | B2 * | 12/2006 | Gysling et al. | 73/32 A |
| 7,171,315 | B2 | 1/2007 | Loose | |
| 7,379,828 | B2 * | 5/2008 | Loose et al. | 702/50 |
| 7,389,187 | B2 * | 6/2008 | Kersey et al. | 702/45 |
| 2002/0129662 | A1 * | 9/2002 | Gysling et al. | 73/861.42 |
| 2004/0199340 | A1 | 10/2004 | Kersey et al. | |
| 2005/0125166 | A1 | 6/2005 | Loose et al. | |
| 2005/0159904 | A1 * | 7/2005 | Loose et al. | 702/45 |

(Continued)

OTHER PUBLICATIONS

GB Search Report, Application No. GB0802061.2, dated Jun. 5, 2008.

*Primary Examiner*—Michael P Nghiem
*Assistant Examiner*—Toan M Le
(74) *Attorney, Agent, or Firm*—Patterson & Sheridan, L.L.P.

(57) ABSTRACT

Methods and apparatus enable sensing flow of a fluid inside a conduit with an array of pressure or strain sensors. Inputs for a curve fit routine include power correlation values at one of multiple trial velocities or speeds of sound and several steps on either side utilizing data obtained from the sensors. The velocity at which a curve fit routine returns a max curvature result corresponds to an estimate value that facilitates identification of a speed of sound in the fluid and/or a velocity of the flow. Furthermore, a directional quality compensation factor may apply to outputs from the curve fit routine to additionally aid in determining the velocity of the flow.

19 Claims, 6 Drawing Sheets

U.S. PATENT DOCUMENTS

2005/0246111 A1* 11/2005 Gysling et al. ............... 702/45
2007/0118304 A1* 5/2007 Loose et al. ................. 702/50
2008/0133182 A1* 6/2008 Gysling ..................... 702/189

* cited by examiner

FLOWMETER ARRAY PROCESSING ALGORITHM WITH WIDE DYNAMIC RANGE

CROSS-REFERENCE TO RELATED APPLICATIONS

This application claims benefit of U.S. provisional patent application Ser. No. 60/888,426, filed Feb. 6, 2007, which is herein incorporated by reference.

BACKGROUND OF THE INVENTION

1. Field of the Invention

Embodiments of the invention generally relate to flow sensing with an array of pressure or strain sensors.

2. Description of the Related Art

A flowmeter consisting of an array of dynamic strain sensors mounted on the exterior of a pipe employs an array processing algorithm applied to signals from the sensors in order to estimate the velocity of pressure waves caused by acoustics in a fluid or turbulent eddies traveling with the fluid passing through the interior of the pipe. In application, time-series sensor signals are transformed to the frequency domain and a velocity reading is calculated by determining the time delay at which the coherence correlation of the sensors is maximized. Selecting a frequency range that includes the majority of the energy created by the pressure waves of interest but avoids spatial aliasing and rejects out-of-band noise can improve performance of the flowmeter.

These frequency limits may correspond to a reduced range of flow rates based on fluid density, such as 0.7 to 10.0 meters per second (m/s) if the expected fluids are liquids (water/oil) or 3.0 to 50.0 m/s if the fluid is mostly gas. However, this approach limits ability to achieve accurate performance over a wide dynamic range of flow velocities using a fixed-length sensor array, and requiring no manual adjustments as is desired. Further, a fixed frequency configuration may yield correct readings for only a very narrow range of flow rates or fail altogether in challenging conditions, such as gas at low flow rates combined with high acoustic noise levels caused by pumps or control valves, for example.

Therefore, there exists a need for an improved flow meter and methods of processing signals from sensors of the meter to determine output values.

SUMMARY OF THE INVENTION

Embodiments of the invention generally relate to flow sensing with an array of pressure or strain sensors coupled to a conduit in which a fluid is flowing. Finding an approximate flow velocity of the fluid begins by dividing a range of possible flow rates into coarse steps with, for example, each approximately 5% higher than the previous one. For each step, a range of frequencies selected for analysis avoids spatial aliasing and common-mode noise. An inverse cross spectral density (CSD) matrix is probed at velocity intervals above and below the coarse step value. In some embodiments, a second-order least-squares curve fit algorithm applied to these points enables determination of the "curvature" of a power correlation around each velocity step. The negative of a second-order coefficient of the curve fit equation may represent the "curvature" value.

A "directional quality" metric may also be calculated for each coarse velocity step by calculating power correlations for the positive and negative directions. The difference of these values is divided by their sum, yielding a number between −1 and 1. Values near zero denote poor quality, where the power in both directions is nearly equal. The absolute value of this quality metric is multiplied by the curvature value, and the velocity at which this product is highest is used as a starting guess in a progressive search routine. A similar approach without the "directional quality" metric facilitates determination of a speed of sound in the fluid.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the invention relate to sensing flow of a fluid with an array of pressure or strain sensors. For some embodiments, the sensing occurs along a conduit carrying hydrocarbons from a producing well such that the sensors may be disposed in a borehole or on production pipe after exiting the borehole. Inputs for a curve fit routine include power correlation values at one of multiple trial velocities or speeds of sound and several steps on either side utilizing data obtained from the sensors. The curve fit routine with a max curvature corresponds to an estimate value that facilitates identification of a speed of sound in the fluid and/or a velocity of the flow. Furthermore, a directional quality compensation factor may apply to outputs from the curve fit routine to additionally aid in determining the velocity of the flow.

Figure 1:
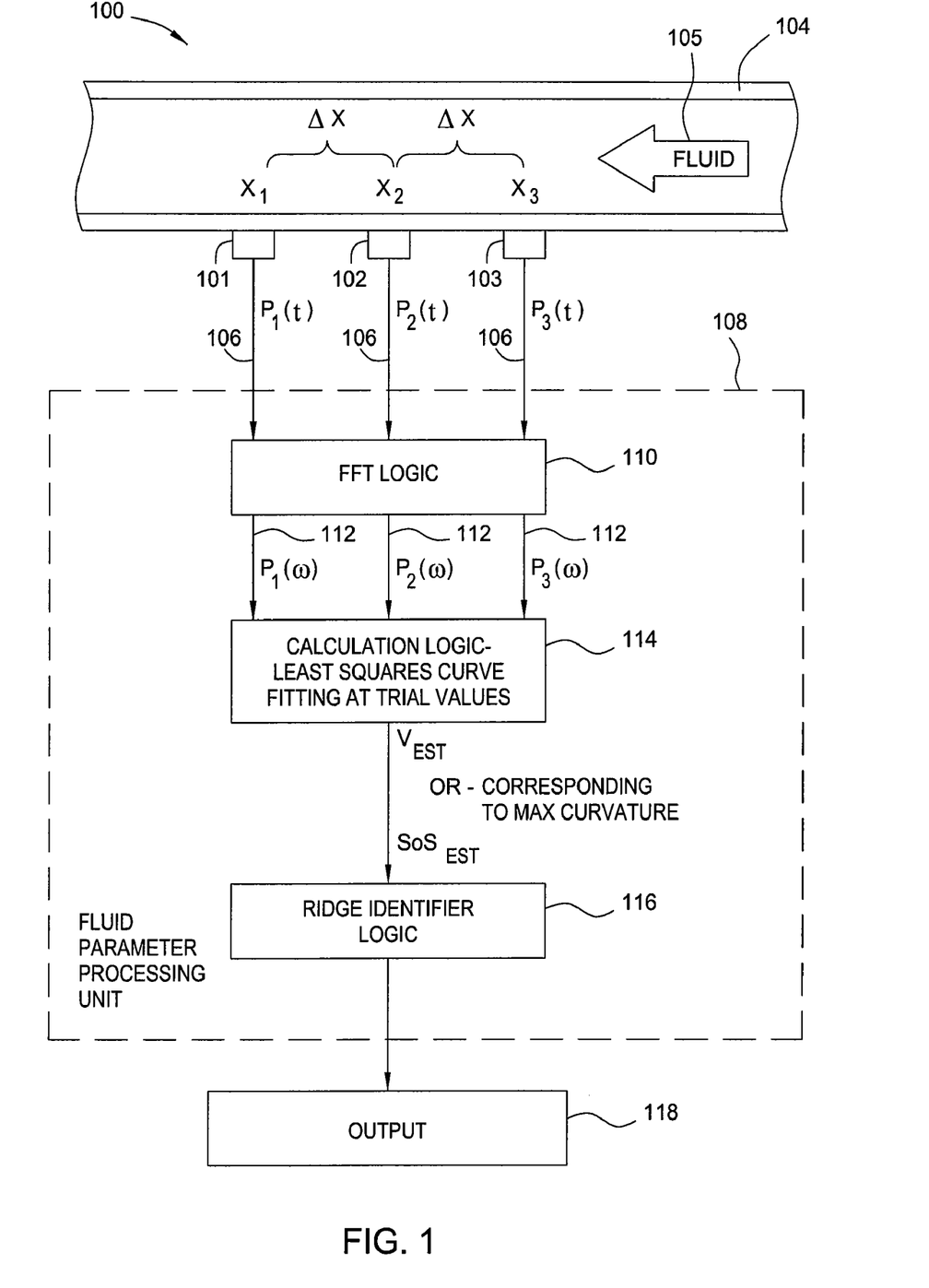
FIG. 1 is a flowmeter including an array of pressure sensors that are coupled to a conduit and a processing unit that is configured to receive signals from the pressure sensors and process the signals, according to embodiments of the invention.

FIG. 1 illustrates a flowmeter 100 that includes first, second and third pressure sensors 101, 102, 103 located respectively at three locations $x_1$, $x_2$, $x_3$ spaced along a conduit 104 such as tubing or a pipe. As described in U.S. Pat. No. 6,354,147, which is herein incorporated by reference, the pressure sensors 101, 102, 103 may include optical fiber wrapped around an outer diameter of the conduit 104, piezoelectric (e.g., polyvinylidene fluoride), capacitive, or resistive measuring devices or other types of optical or electrical strain gauges. The pressure sensors 101, 102, 103 provide pressure time-varying signals $P_1(t)$, $P_2(t)$, $P_3(t)$ on lines 106 to a fluid parameter processing unit 108 of the flowmeter 100 for accomplishing functions, which may be implemented in software (using a microprocessor or computer) and/or firmware, or may be implemented using analog and/or digital hardware, having sufficient memory, interfaces, and capacity to perform the functions described herein. In some embodiments, physical computer readable storage medium of the processing unit 108 may contain instructions for such functions.

The flowmeter 100 enables measuring one or both of two fundamental parameters that directly relate to the flow properties of a fluid 105 and include (1) the speed at which pressure waves propagate through the fluid 105, the speed of sound (SoS), and (2) the convection velocity of the fluid 105. These values can be determined by measuring dynamic pressures in the fluid using the pressure sensors 101, 102, 103. Dynamic pressure measurements from the sensors 101, 102, 103 are then processed utilizing array processing techniques to extract at least one of the speed of sound and the flow velocity. The flowmeter 100 may consist of either (1) a single array of the sensors 101, 102, 103 that are equally spaced or (2) two arrays with different spacing (i.e., one spacing for measuring the speed of sound and another spacing for measuring vortical velocity). If the speed-of-sound sensor spacings are chosen to be an integer multiple of the vortical velocity array spacing, then the two arrays may share sensors. In some embodiments, each array may contain fewer or more than the first, second and third sensors 101, 102, 103.

While the acoustic pressure disturbances move through the fluid 105 at the speed of sound, the vortical pressure disturbances move with the fluid 105 at the flowing velocity. In addition, the acoustic pressure disturbances propagate through the flowmeter 100 in both directions assuming there are acoustic sources on both sides of the flowmeter 100 or acoustic reflections, while the vortical pressure disturbances propagate through the flowmeter 100 only in one direction, which is the flowing direction. However, both the acoustic and vortical pressure disturbances strain the wall of the conduit 104 independently and simultaneously and so the signal measured by the sensors 101, 102, 103 contains a superposition of both these signals (and possibly others such as vibration). The amplitude of the vortical signal may be much less than the acoustic signal, so there may be a need to reduce the acoustic part of the overall signal such that the vortical part is exposed. Processing of vortical and acoustic pressure signals may thus require different treatment even though the same basic processing method is used for both.

The processing unit 108 includes Fast Fourier Transform (FFT) logic 110 that initially receives the pressure time-varying signals $P_1(t)$, $P_2(t)$, $P_3(t)$ from the pressure sensors 101, 102, 103. The FFT logic 108 calculates the Fourier transform of blocks of data from the time-based input signals $P_1(t)$, $P_2(t)$, $P_3(t)$ of individual ones of the sensors 101, 102, 103 and provides complex frequency domain (or frequency based) signals $P_1(\omega)$, $P_2(\omega)$, $P_3(\omega)$ on lines 112 indicative of the frequency content of the input signals. Because the vortical flow velocity is derived from a lower frequency range than the speed-of-sound, larger block sizes may be used for the vortical velocity, providing more resolution in that frequency range. Instead of FFT's, any other technique for obtaining the frequency domain characteristics of the pressure time-varying signals $P_1(t)$, $P_2(t)$, $P_3(t)$ may be used. For example, a cross-spectral density (CSD) and power spectral density may be used to form a frequency domain transfer function or frequency response or ratios.

For the flow velocity processing, differencing adjacent ones of the sensors 101, 102, 103 can subtract common-mode noise and reduce the number of signals, N, by one. Once transformed into the frequency domain, a CSD function is applied resulting in a complex N×N matrix for each frequency bin produced by the transform, where N is the number of the sensors 101, 102, 103 in the array minus one. Each N×N matrix is then inverted. As explained further herein, probing this set of inverted matrices occurs using the processing unit 108 to produce curvatures corresponding to trial velocities in a first pass of the matrix with calculation logic 114. The processing unit 108 further may fine tune a result based on the curvatures during subsequent passes at increasingly finer resolution with ridge identifier logic 116. An output 118 of the processing unit 108 may communicate the result (e.g., the velocity and/or the speed of sound) to a user via, for example, a display or printout. Further, the output 118 may generate a signal or control a device based on the result.

Figure 2:
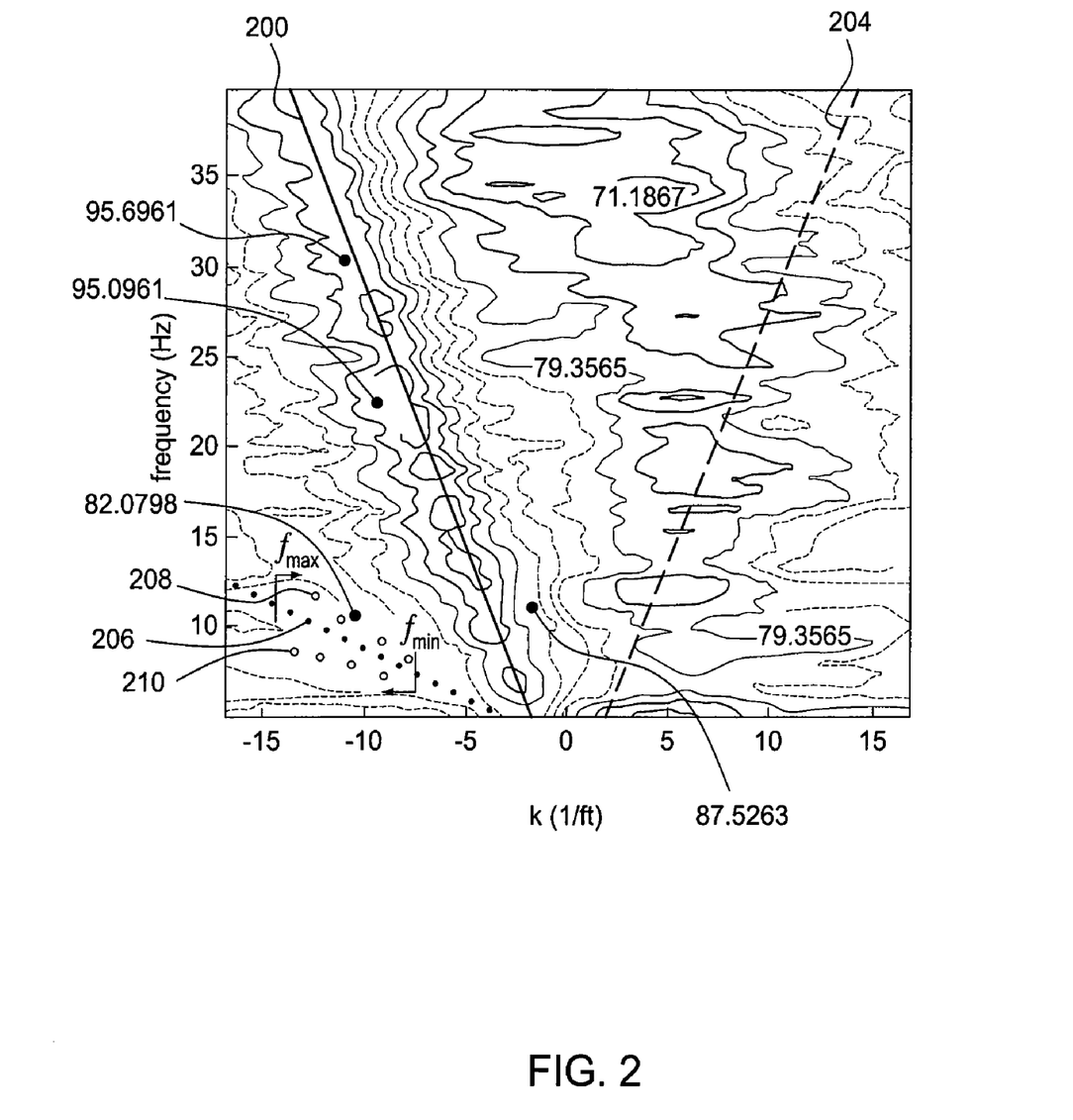
FIG. 2 is a k-ω (wave number-frequency) plot graphically representing data generated by the pressure sensors and from which a velocity of flow through the conduit may be derived, according to embodiments of the invention.
Figure 3:
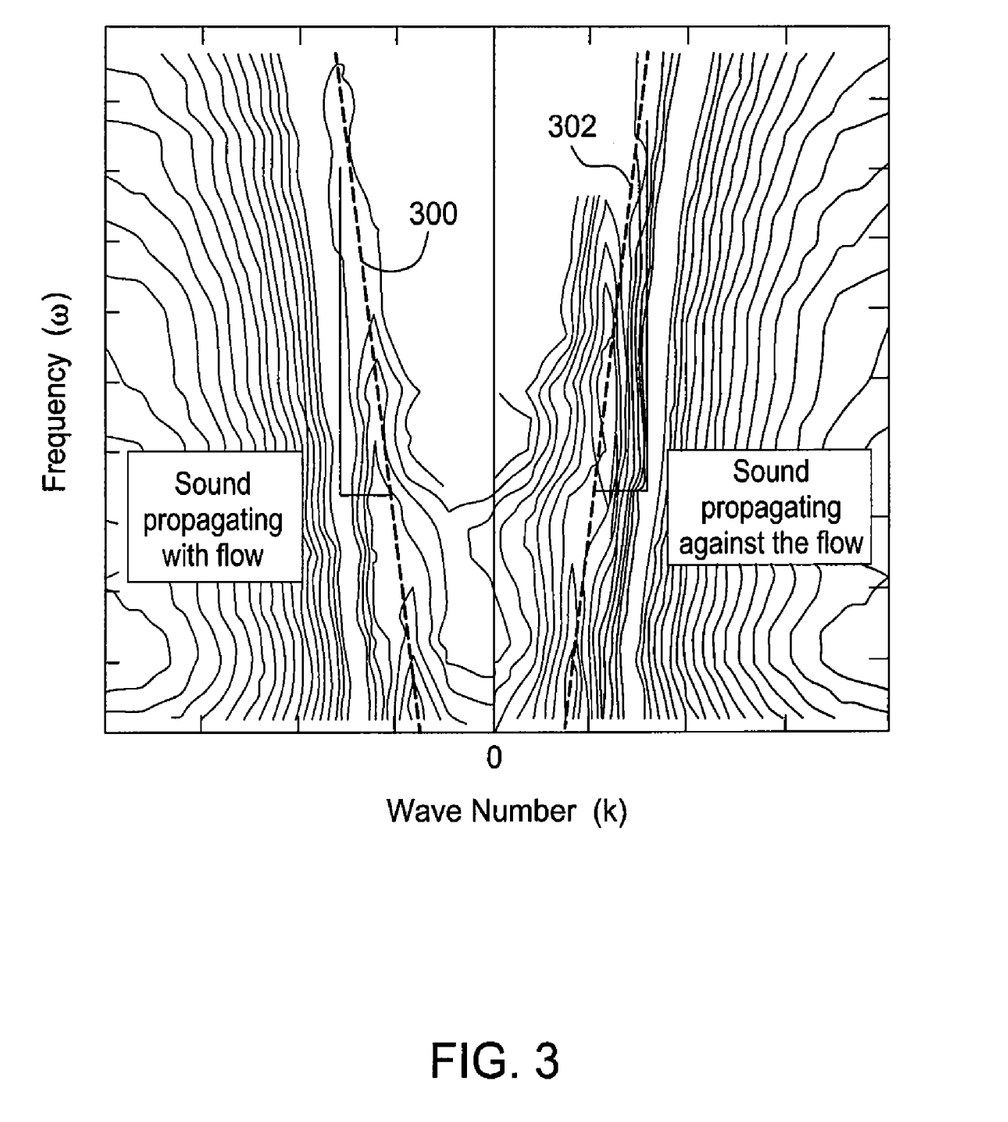
FIG. 3 is another k-ω plot graphically representing data generated by the pressure sensors and from which a speed of sound in fluid inside the conduit may be derived, according to embodiments of the invention.

FIGS. 2 and 3 illustrate three dimensional k-ω plots employed to visualize the contents of the inverse CSD matrix. FIG. 2 depicts a ridge of increased power around flow velocity line 200 corresponding to a velocity of the flow while FIG. 3 shows ridges of increased power around sound velocity lines 300, 302 associated with the speed of sound. These FIGS. 2 and 3 depict plots of the power correlation of the inverse CSD matrix as a function of frequency ω and wave number k (phase shift) with relative power of certain contour lines identified only in FIG. 2 for illustration purposes. Slopes of the lines 200, 300, 302 reveal respective velocities (V) according to the following equation:

$$V = \frac{\omega}{k} = \frac{2\pi f}{k}.$$

Output from a Capon algorithm scan of the inverse CSD matrix shows velocity versus power by sampling power correlations through a range of velocities. Several other array processing algorithms exist (e.g. cross correlation Beam scan, MUSIC, ESPRIT, etc) and may be implemented with embodiments described herein instead of the Capon. Evaluation of locations on the plots in FIGS. 2 and 3 that yield maximum power correlation values with the Capon search alone and without any initial estimates identifies the lines 200, 300, 302 under only some conditions but tends to fail or become unreliable in other applications in which the flowmeter 100 may be utilized. In some cases, a first pass of the Capon algorithm (see, FIG. 7) alone over a wide dynamic range (e.g., two orders of magnitude) may produce multiple peaks obscuring a true peak. Further, low frequency noise and speed of sound velocities may additionally prevent distinguishing a relatively weaker vortical ridge having a peak that is not associated with the maximum power correlation.

Figure 4:
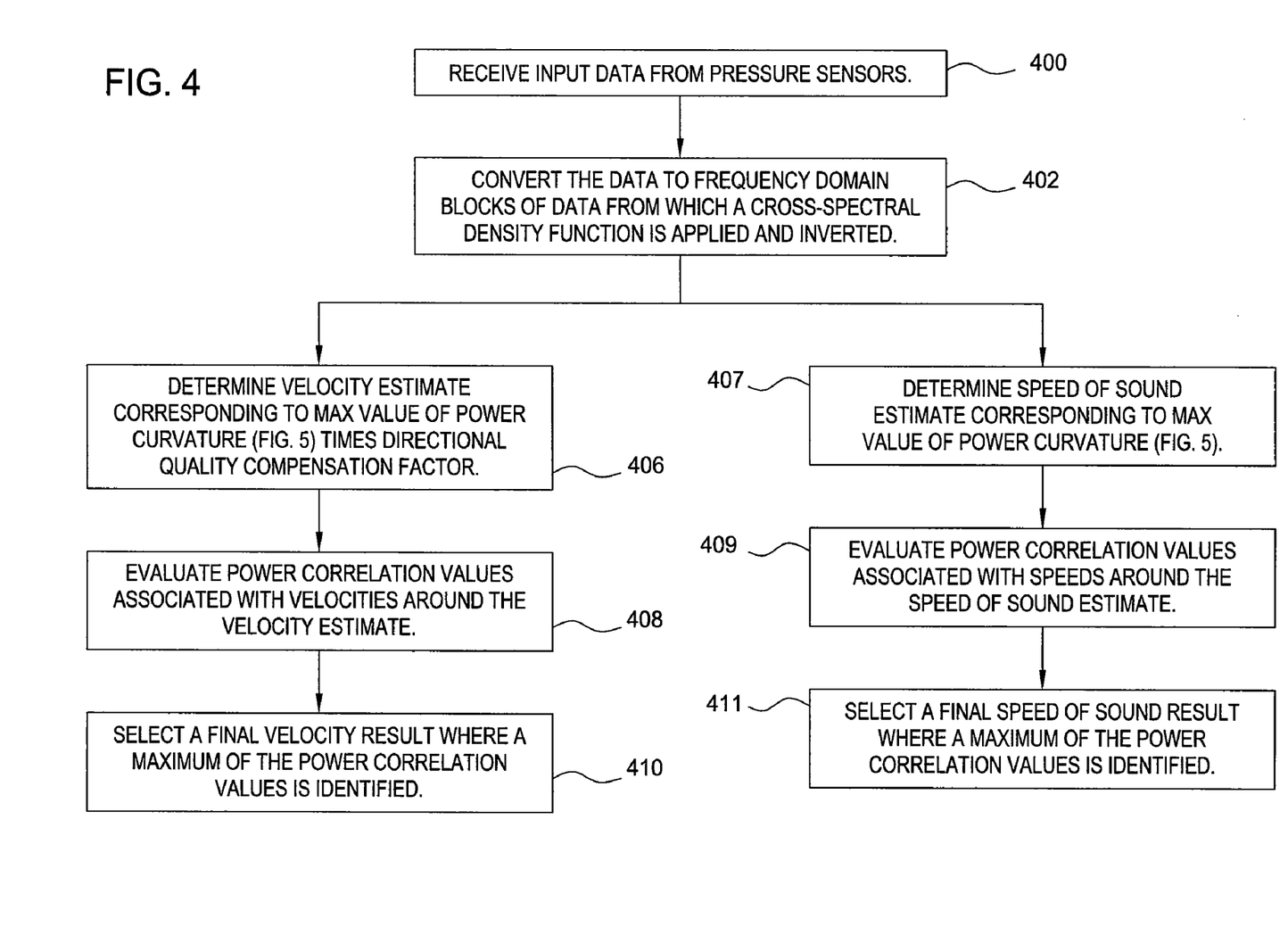
FIG. 4 is a flow diagram illustrating methods of determining the velocity and speed of sound according to embodiments of the invention.

Therefore, FIG. 4 illustrates sensing methods performed with the processing unit 108 for determining speed of sound and flow velocity that improve ability to identify the lines 200, 300, 302. As with prior approaches, signal entry step 400 involves receiving input data from the pressure sensors 101, 102, 103 so that initial processing step 402 can convert, with the FFT logic 110, the data to frequency domain blocks of data and subsequently apply and thereafter invert a CSD function. In both velocity and speed of sound estimation steps 406, 407, calculation logic 114 then probes matrices produced in the initial processing step 402 using, for example, the Capon method to measure the power correlation of the signals at time shifts associated with an identified velocity or speed of sound. In other words, the time shift as related to flow velocity refers to the fact that a particular power phenomena received at the third sensor 103 from the fluid 105 is received later in time at the second sensor 102 as the fluid 105 flows from the third sensor 103 to the second sensor 102. For some embodiments, the velocity estimation step 406 processes a first subset of vectors corresponding to the velocity while a second subset of sensor data related to the speed-of-sound is passed to the speed of sound estimation step 407. Inputs for a curve fit routine (see, FIG. 5) include power correlation values at one of multiple trial velocities or speeds of sound and several steps on either side utilizing data obtained from the sensors 101, 102, 103. The velocity at which the curve fit routine returns a maximum curvature result corresponds to an estimate value of a speed of sound in the fluid and/or a velocity of the flow.

For the velocity estimation step 406, multiplying results of the curve fit routine for each trial velocity by a respective directional quality compensation factor ($Q_{trial}$) calculated at each trial value helps to avoid misidentification of noise appearing symmetrically in both positive and negative directions instead of the vortical ridge since the vortical ridge extends in only one direction. Referring to FIG. 2, differences in power along the flow velocity line 200 with respect to a positive and directionally opposite dashed line 204 indicates that the power along the flow velocity line 200 is not attributed to symmetrical noise. As symmetry in power between positive and negative directions decreases, the compensation factor or an absolute value of the factor approaches one, while the compensation factor goes to zero with increasing symmetry. Therefore, the product of the directional quality compensation factor and the power curvature for each trial value adjusts the results of the curve fit routine prior to determining the velocity estimate corresponding to this product. For some embodiments, a ratio of the difference and the sum of a first power correlation function $P(V_{trial})$ for a given velocity trial and a second power correlation function $P(-V_{trial})$ for an opposite velocity negative of the given velocity trial defines the directional quality compensation factor as follows:

$$Q_{trial} = \frac{P(V_{trial}) - P(-V_{trial})}{P(V_{trial}) + P(-V_{trial})}.$$

When a velocity quality metric such as the directional quality compensation factor falls below values of approximately 0.4 at the velocity estimate, any flow velocity calculation results may lack sufficient confidence levels. The software in the processing unit 108 may thus include a low-quality cutoff setting. With this cutoff, a reported value of zero or error at the output 118 may occur if the velocity quality metric is below a configured limit.

To ensure quality in the results for speed of sound, a speed of sound quality metric may yield a similar range of values as the directional quality compensation factor. Values for speed of sound quality ($Q_{curv}$) approach one for high values of curvature when $$Q_{curv} = \frac{C}{\text{abs}(C)} \times e^{(-50/abs(C))},$$

where C is a coefficient in a least squares equation described further herein. The speed of sound quality metric includes an arbitrary value of fifty which is near the lower limit for the "acceptable" range of curvature values. A low quality cutoff for reporting purposes may be around 0.3 or about 0.25 at the speed of sound estimate.

Once the curvature in power as a function of each of the velocity trials reveals the approximate location of a power peak that corresponds to the flow velocity estimate or speed of sound estimate, a conventional array processing algorithm may evaluate with the ridge identifier logic 116 power correlation values associated with velocities or speeds around the velocity estimate or the speed of sound estimate in refining velocity and speed of sound steps 408, 409. In some embodiments, the power correlation of the frequency to wave number domain is evaluated via Capon routines at a finer resolution relative to increments between trial velocities and over a range of ±20% relative to the estimates. If a new-found power peak from this subsequent scan differs by more than half the increment size, then the set of frequencies used is adjusted to coincide with the new-found peak. The velocity having the highest power result is used as the center for the next pass of power correlations at an even finer resolution. For example, this refinement process may repeat three times, with the velocity increment size reduced by a factor of eight for each repetition. At the end of this refinement, velocity and speed of sound output steps 410, 411 select a final velocity and speed of sound associated with maximums of the power correlation value from a last scan. The output 118 then indicates the final velocity and/or speed of sound to the user or another device.

Figure 5:
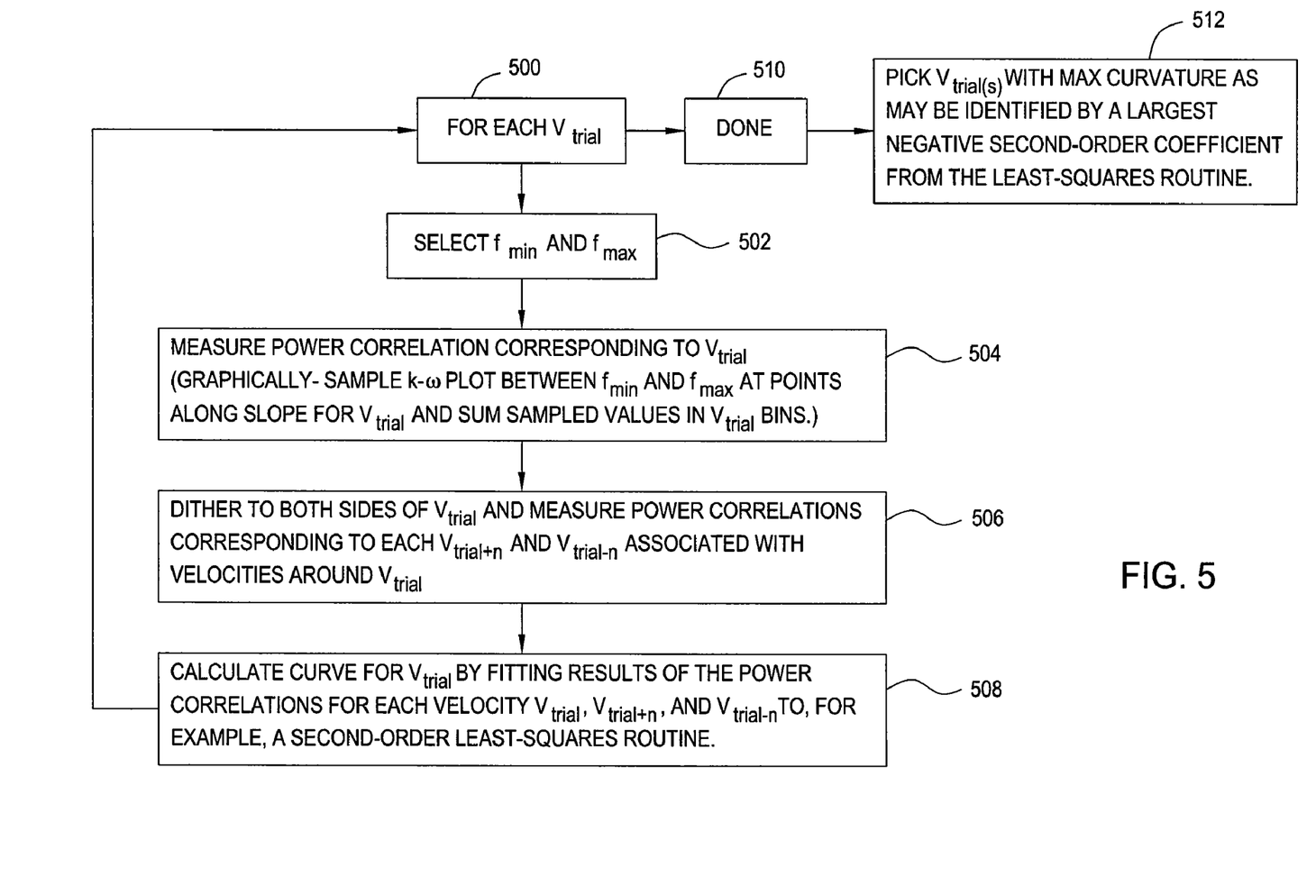
FIG. 5 is another flow diagram illustrating a process of determining an initial velocity (or speed of sound) estimate utilized in the methods depicted by FIG. 4, according to embodiments of the invention.

FIG. 5 shows a process of determining the velocity (which may be the vortical flow or the speed of sound) estimate utilized in the estimation steps 406, 407. Multiple trial velocities ($V_{trials}$) selected in a first pass step 500 identifies selected velocities at increments of, for example, 5% through an entire range of possible velocities. The frequency range dynamically reflects changing velocity conditions. For an array with sensor spacing $\Delta x$, the spatial aliasing frequency (spatial Nyquist) for velocity is given by:

$$f_N = \frac{V}{\Delta x}.$$

The frequency range set in a frequency selection step 502 corresponds to a fraction of this Nyquist frequency to avoid aliasing and common-mode signals. In some embodiments, these fractional amounts may identify minimum and maximum frequencies for all power correlations associated with each respective $V_{trial}$ picked for the vortical flow with $$f_{min}=0.3f_N \text{ and } f_{max}=0.7f_N.$$

The frequency range explored by the power correlations for the speed of sound may also vary to adapt for each of the $V_{trials}$. Range of acoustic frequencies measured depends on the sensor array dimensions and the speed of sound in the fluid as follows:

$$\lambda_{max} = K \times L \Rightarrow f_{min}$$
$$= \frac{SoS}{\lambda_{max}}$$
$$= \frac{1}{K \times N} f_N \to f_{min}$$
$$= .083 f_N$$

and $$\lambda_{min} = 2 \times \Delta x \Rightarrow f_{max} = \frac{SoS}{\lambda_{min}} = .5 f_N,$$

where K is a factor such as 4 or 5 that determines the largest measurable wavelength, L is the aperture length between most upstream and most downstream sensor (as shown, the third sensor 103 and the first sensor 101) with N being the number of sensors (as shown, three), and the factor two in the expression being a Nyquist based factor. The frequency selection step 502 thus may set appropriate limits in terms of the spatial Nyquist frequency for the sensor spacing and $V_{trial}$ in speed of sound determinations as with the flow velocity determinations.

Once the frequency range is set for a first $V_{trial}$, initial power correlation step 504 measures the magnitude of the power corresponding to the first $V_{trial}$ within the frequency limits. The initial power correlation step 504 involves sampling and summing spaced frequency bins between the $f_{min}$ and $f_{max}$ for the first $V_{trial}$. Graphically, FIG. 2 shows a solid dotted line 206 representing the first $V_{trial}$. Some of the dots may symbolize these bins along the slope for the first $V_{trial}$.

Next, additional power correlations step 506 samples and sums the same set of frequency bins, in some embodiments, as utilized in the initial power correlation step 504 at several (e.g., about 7 to 9) velocity increments ($V_{trial+n}$, $V_{trial-n}$) on either side of the first $V_{trial}$. This technique may be referred to as "dithering" or "jittering" the velocity of each $V_{trial}$. For some embodiments, selection of the velocity increments equally spaces all velocity increments from one another. The velocity increments may span a range suitable to detect sharp falloffs on either side of a peak, such as 90% to 110% of each $V_{trial}$. Since this increment range is identified as a percentage of the $V_{trial}$, the effects from power correlation ridge width differences at lower versus higher flow velocities tends to be equalized, yielding similar curvature values at all velocities. With respect to FIG. 2, maintaining the same frequencies and hence adjusting wave number produces slopes and frequency bins such as represented by first and second open dotted lines 208, 210 that may correspond respectively to one of the $V_{trial+n}$ and one of the $V_{trial-n}$.

Curvature step 508 fits results from the initial power correlation step 504 and the additional power correlations step 506 to a curve based on power correlation values measured at the first $V_{trial}$ and each of the $V_{trial+n}$, $V_{trial-n}$ associated with the first $V_{trial}$. Inputs from all $V_{trials}$ selected in the first pass step 500 thereby result in generation of multiple independent curves at the curvature step 508 with a corresponding curve for each $V_{trial}$. For some embodiments, a second-order least-squares curve fit routine, such as $$y=a+b*x+c*x^2,$$

where y represents power inputs and x corresponds to velocity inputs, enables calculating curvature values, which correspond to respective ones of the trial velocities. In some embodiments, each least squares curve fit is calculated using "normalized" (x,y) coordinates instead of what would be the "true" coordinates. Using the "true" coordinates may yield curvature values that are higher at low velocities than at high velocities. Referring back to FIG. 1, the calculation logic 114 determines a negative of this "curvature" of power functions evaluated around each corresponding trial velocity by, for example, defining the "c" coefficient of the curve fit routine as a curvature value.

An end step 510 recognizes when all the multiple trial velocities identified and selected in the first pass step 500 have been interrogated and hence all curves generated in the curvature step 508. A ridge peak velocity for speed of sound or vortical flow occurs close to the largest negative curvature value which is associated with one of the trial velocities. From the curves, estimation output step 512 thus picks one (or two, i.e., positive and negative, in the case of speed of sound) of the trial velocities with a max curvature or curvature value, as may be identified by the negative of the "c" coefficient. As previously discussed, the curvature values may be multiplied by the directional quality compensation factor prior to picking the trial velocities with a maximum calculated value. Regardless, picked $V_{trial(s)}$ establish the velocity estimate or the speed of sound estimate.

For some embodiments, a prior final velocity from a previous measurement in time utilized for a current estimate enables truncation of the methods described herein once an initial measurement is taken as discussed heretofore. For example, the prior final velocity may provide the current estimate unless a quality metric returns below a threshold. In some embodiments, the prior final velocity may enable establishing a relatively narrower range of velocities scanned in the first pass step 500 than searched in the previous measurement.

For visualization, the curve associated with the first $V_{trial}$ represented by the solid dotted line 206 in FIG. 2 produces a relatively low curvature compared to that of the flow velocity line 200 as there is no significant pattern among differences in power between any of the dotted lines 206, 208, 210. The directional quality metric further reduces any curvature present as calculated for the first $V_{trial}$ represented by the solid dotted line 206 due to substantial symmetrical noise also present oppositely in the positive direction. Even when conventional power correlation scanning alone may fail to identify or accurately identify velocities, max curvature based analysis of trial velocities enables a less obscured and more accurate determination of vortical velocity or speed of sound.

Figure 6:
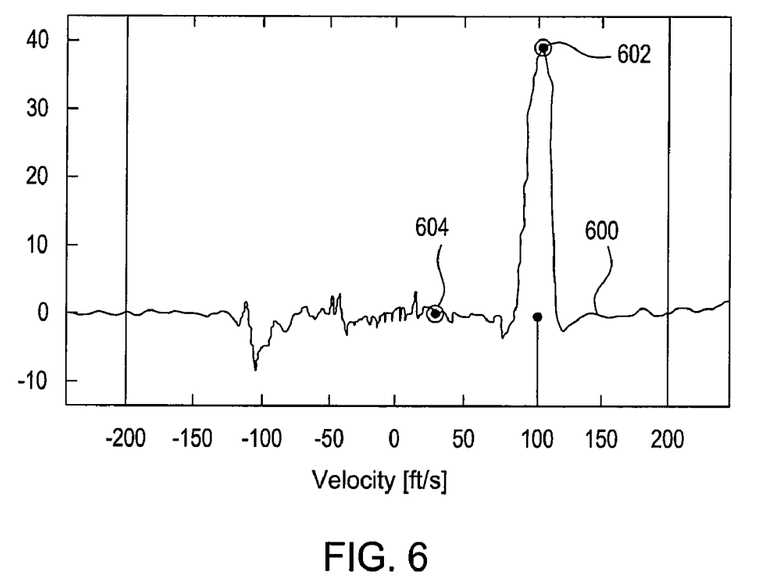
FIG. 6 is a plot of products obtained by multiplying a respective directional quality compensation factor times a max value of power curvature for each velocity step evaluated according to the process depicted in FIG. 5 versus velocity.

FIG. 6 shows an estimation curve 600 that plots products obtained by multiplying a respective directional quality compensation factor times a max value of power curvature for each velocity step evaluated according to the process depicted in FIG. 5 versus velocity. A low value product point 604 lacks one or both of unidirectionality or a high curvature value similar to the first $V_{trial}$ represented by the solid dotted line 206 in FIG. 2. By contrast, a high value product point 602 derives from a high curvature value, similar to one taken at flow velocity line 200, which is not negated by the directional quality compensation factor being indicative of high symmetry.

Figure 7:
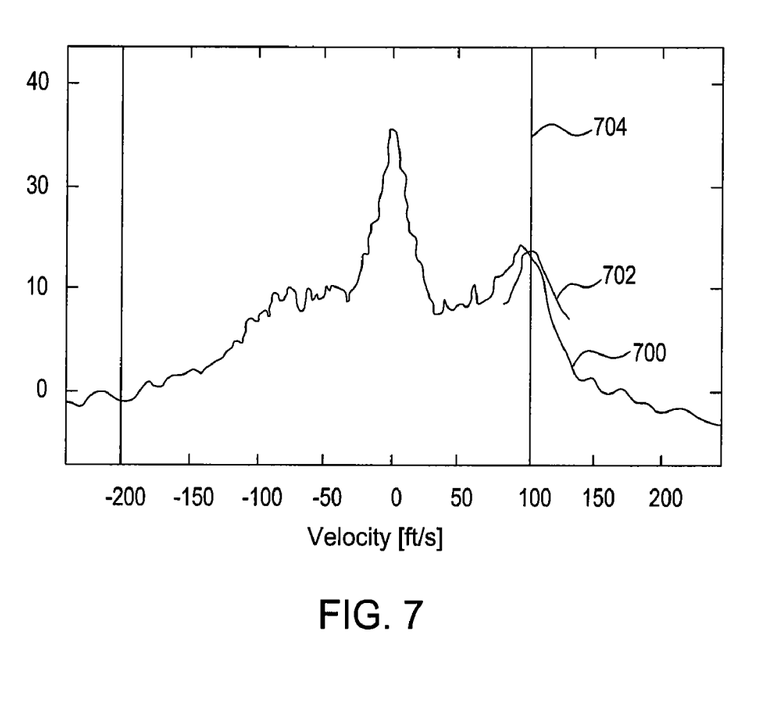
FIG. 7 is a plot of power versus velocity, which is obtained by a total scan of converted data from the sensors and a targeted scan of the converted data around the velocity estimate picked by results plotted in FIG. 6 to identify a final velocity utilizing a peak of the targeted scan.

FIG. 7 illustrates a plot of power versus velocity showing a total scan curve 700 which is obtained by searching converted data from pressure sensors and a targeted scan curve 702 of the converted data around a velocity estimate picked by results plotted in FIG. 6 to identify a final velocity 704 at a peak centered at 103 feet per second. The total scan curve 700 includes multiple peaks with the peak of the final velocity not being a maximum peak thereby obscuring results taken from the total scan curve 700 alone. However, identification of the peak of the final velocity appears clear and distinct in FIG. 6 even though FIGS. 6 and 7 are plots taken based on the same fluid flow.

For reference, the estimation curve 600 in FIG. 6 corresponds to data evaluated in the calculation logic 114 in FIG. 1 and utilized in the velocity estimation step 406 in FIG. 4 as derived from the process in FIG. 5. The estimation curve 600 replaces the total scan curve 700 that is not required and is only shown for illustration purposes. Further, the targeted scan curve 702 represents data used in the refining velocity step 408 in FIG. 4 and examined in the ridge identifier logic 116 in FIG. 1.

While the foregoing is directed to embodiments of the present invention, other and further embodiments of the invention may be devised without departing from the basic scope thereof, and the scope thereof is determined by the claims that follow.

What is claimed is:

1. A sensing system for measuring a flow velocity of a fluid in a conduit, comprising:
    an array of at least two pressure sensors spaced along the conduit to output signals indicative of dynamic pressure variations of the fluid; and
    a signal processor configured to process the signals by probing trial velocities, wherein the probing includes calculating power curvatures associated with power correlations of the signals determined around the trial velocities and selecting one of the trial velocities corresponding to a maximum curvature value from the power curvatures as a measurement for the flow velocity, wherein the signal processor further applies a respective directional velocity quality metric to adjust power curvature values from each of the power curvatures by multiplying the respective directional velocity quality metric with the power curvature values from each of the power curvatures.

2. The sensing system of claim 1, wherein the probing further comprises for each trial value selecting minimum and maximum frequencies that remain constant for all of the power correlations used to derive one of the curvatures.

3. The sensing system of claim 1, wherein the probing further comprises calculating the curvatures by fitting data from the power correlations to a least squares polynomial.

4. The sensing system of claim 3, wherein the polynomial is defined as $y = a + b*x + c*x^2$, wherein "y" represents a power input, "x" corresponds to a velocity input, and "a," "b," and "c" are coefficients, with the maximum curvature value being a negative of the "c" coefficient that is greatest.

5. The sensing system of claim 1, wherein the signal processor further applies the respective directional quality metric based on symmetry of power in negative and positive directions prior to selecting one of the trial velocities corresponding to the maximum curvature value.

6. The sensing system of claim 1, wherein the signal processor is configured to further process the signals by scanning final velocity power correlations within a percentage of the measurement for the flow velocity and at a finer resolution than the probing such that a ridge identified in the scanning corresponds to a final value of the flow velocity.

7. The sensing system of claim 1, wherein the signal processor is further configured to probe trial speeds of sound by calculating curvatures associated with power correlations of the signals determined around the trial speeds of sound and selecting a positive and a negative one of the trial speeds of sound corresponding to a respective maximum curvature value from the curvatures associated with a positive direction and from the curvatures associated with a negative direction.

8. A sensing system for measuring a parameter of a fluid in a conduit, comprising:
    an array of at least two pressure sensors spaced along the conduit to output signals indicative of dynamic pressure variations of the fluid; and
    a signal processor configured to process the signals by probing trial velocities, wherein the probing includes calculating power curvatures associated with power correlations of the signals determined around the trial velocities and selecting one of the trial velocities corresponding to a maximum curvature value from the power curvatures as a measurement for the parameter, wherein the signal processor further applies a velocity quality metric to adjust power curvature values from each of the power curvatures by multiplying the velocity quality metric with the power curvature values from each of the power curvatures.

9. The sensing system of claim 8, further comprising an output to communicate the measurement for the parameter.

10. The sensing system of claim 9, wherein the signal processor only provides the measurement for the parameter to the output if a result from the quality metric is above a threshold value.

11. The sensing system of claim 8, further comprising a display configured to show at least one of a speed of sound in the fluid and a flow velocity of the fluid as determined based on the measurement for the parameter.

12. A sensing system for measuring a parameter of a fluid in a conduit, comprising:
    an array of at least two pressure sensors spaced along the conduit for outputting signals indicative of dynamic pressure variations of the fluid; and
    a signal processor configured to process the signals by performing a method of probing the signals at first and second trial velocities that includes:
    measuring first power correlations corresponding to the first trial velocity and first incremental velocities on either side of the first trial velocity to produce first data of the first power correlations;
    measuring second power correlations corresponding to the second trial velocity and second incremental velocities on either side of the second trial velocity to produce second data of the second power correlations;
    calculating first and second curvatures for the first and second data, respectively;
    applying a velocity quality metric to adjust curvature values from the first and second curvatures by multiplying the velocity quality metric with the curvature values from the first and second curvatures;
    selecting which one of the first and second trial velocities corresponds to a greater of the first and second curvatures based on the adjusted curvature values and represents an estimate value for the parameter; and outputting the estimate value.

13. The sensing system of claim 12, wherein the parameter is at least one of a flow velocity of the fluid and a speed of sound in the fluid.

14. The sensing system of claim 12, wherein calculating each of the curvatures occurs by fitting a respective one of the data to a least squares polynomial.

15. A method of measuring a parameter of a fluid in a conduit, comprising:
    sensing at spaced locations along the conduit dynamic pressure variations of the fluid to provide signals indicative of the pressure variations;
    processing the signals by probing trial velocities, wherein the probing includes calculating power curvatures associated with power correlations of the signals determined around the trial velocities and selecting one of the trial velocities corresponding to a maximum curvature value from theob rcurvatures as a measurement for the parameter, wherein the processing further includes applying a velocity quality metric to adjust power curvature values from each of the power curvatures by multiplying the velocity quality metric with the power curvature values from each of the power curvatures; and outputting the measurement for the parameter to a display.

16. The method of claim 15, wherein outputting the measurement for the parameter provides an estimate for further processing of the signals.

17. The method of claim 15, further comprising outputting a flow velocity of the fluid to the display based on the measurement for the parameter.

18. The method of claim 15, further comprising outputting a speed of sound in the fluid to the display based on the measurement for the parameter.

19. The method of claim 15, further comprising selecting for each trial value minimum and maximum frequencies that remain constant for all of the power correlations used to derive one of the curvatures.

\* \* \* \* \*

UNITED STATES PATENT AND TRADEMARK OFFICE
CERTIFICATE OF CORRECTION

PATENT NO. : 7,881,884 B2  Page 1 of 1
APPLICATION NO. : 12/025294
DATED : February 1, 2011
INVENTOR(S) : Perry et al.

It is certified that error appears in the above-identified patent and that said Letters Patent is hereby corrected as shown below:

In the Claims:

Column 11, Claim 15, Line 4, please delete "theob rcurvatures" and insert --the power curvatures-- therefor.

Signed and Sealed this
Sixth Day of September, 2011

David J. Kappos
*Director of the United States Patent and Trademark Office*